United States Patent
Bournay et al.

(10) Patent No.: US 6,878,837 B2
(45) Date of Patent: Apr. 12, 2005

(54) PROCESS FOR PRODUCING ALKYL ESTERS FROM A VEGETABLE OR ANIMAL OIL AND AN ALIPHATIC MONOALCOHOL

(75) Inventors: Laurent Bournay, Lyons (FR); Gerard Hillion, Herblay (FR); Pierre Boucot, Ternay (FR); Jean-Alain Chodorge, Antony (FR); Charles Bronner, Irigny (FR); Alain Forestiere, Vernaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/411,384

(22) Filed: Apr. 11, 2003

(65) Prior Publication Data

US 2004/0034244 A1 Feb. 19, 2004

(30) Foreign Application Priority Data

Apr. 11, 2002 (FR) ............................................ 02 04565

(51) Int. Cl.[7] .............................................. C07C 51/00
(52) U.S. Cl. ...................................... 554/169; 554/167
(58) Field of Search ................................. 554/167, 169

(56) References Cited

U.S. PATENT DOCUMENTS 5,908,946 A * 6/1999 Stern et al. ................. 554/167
6,262,285 B1 7/2001 McDonald

FOREIGN PATENT DOCUMENTS

| EP | 0200982 A | 11/1986 |
|----|-----------|---------|
| FR | 2752242 A | 2/1998 |
| FR | 2752242 * | 2/1998 |

OTHER PUBLICATIONS

XP-002170978—JAOCS, vol. 61, No. 10 (Oct. 1984), "Rapeseed Oil Transesterification By Heterogeneous Catalysis", G.R. Peterson et al. pp. 1593–1597.

* cited by examiner

*Primary Examiner*—Deborah D. Carr
(74) *Attorney, Agent, or Firm*—Millen, White, Zelano & Branigan, P.C.

(57) ABSTRACT

Alkyl esters of fatty acids, and high purity glycerin, are produced using a process comprising a set of transesterification reactions between a vegetable or animal oil and an aliphatic monoalcohol employing a heterogeneous catalyst, for example based on zinc aluminate, the water content in the reaction medium being controlled to a value that is below a given limiting value.

21 Claims, 1 Drawing Sheet

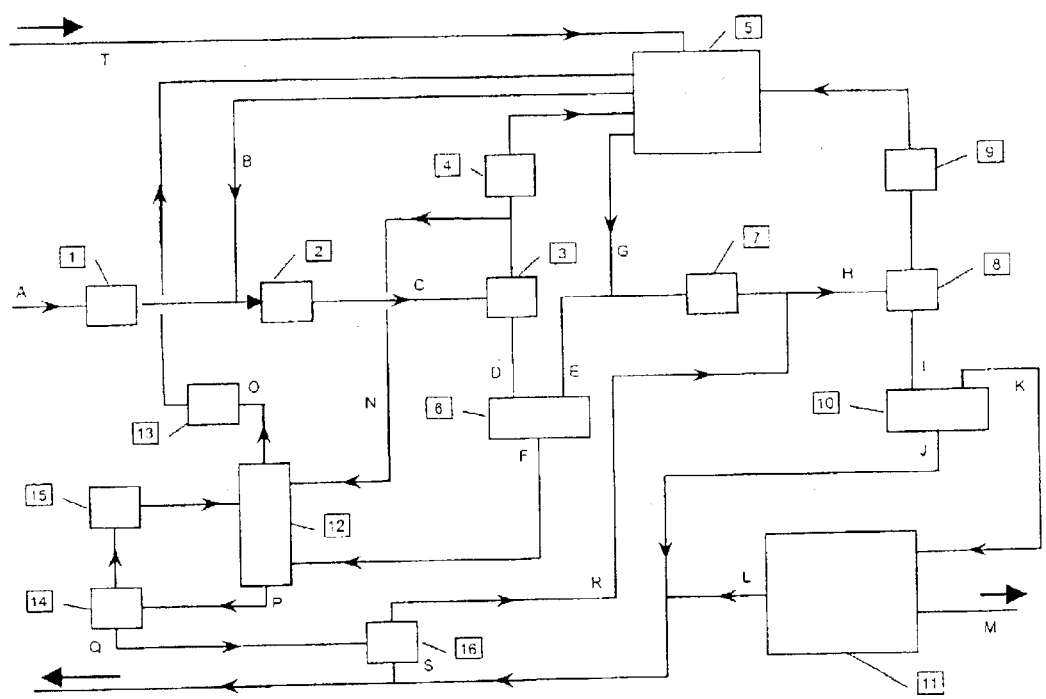

PROCESS FOR PRODUCING ALKYL ESTERS FROM A VEGETABLE OR ANIMAL OIL AND AN ALIPHATIC MONOALCOHOL

BACKGROUND OF THE INVENTION

Field of the Invention

The invention relates to the production of alkyl esters derived from vegetable or animal oils, in particular methyl esters derived from rapeseed oil.

The use of vegetable oil methyl esters (VOME) as fuel substitutes is set for major development over the next few decades. The presence of trace amounts of monoglycerides in those products (maximum of 0.8% by weight according to the current standard) advantageously compensates for the loss in lubricating power primarily due to a reduction in the sulfur content of the gas oil. The sulfur content will be limited to 50 ppm by weight in 2005 and to 10 ppm by weight in 2008. Further, the European Commission has adopted a plan of action and two directives have been proposed that encourage the use of substitute fuels in the transport sector, starting with regulations and fiscal measures intended to promote biofuels. The plan of action defines a strategy that between now and 2020 will replace 20% of diesel fuel and gasoline by substitute fuels in the road transport sector. One of the proposed directives envisages that biofuels will represent a minimum proportion of 2% of all of the fuel sold from 2005, a minimum which will attain 5.75% by 2010. The production of methyl esters derived from vegetable oils (usually termed Biodiesel), essentially from rapeseed oil, exceeds 300000 tons/year in France. Further, there are other possible applications for said products, such as ecological solvents and base compounds for the production of sulfonates of fatty alcohols, amides, ester dimers, etc.

Processes for producing alkyl esters (for example methyl esters) have already been developed. They use conventional homogeneous catalysis techniques with soluble catalysts such as sodium hydroxide or sodium methylate by reacting a neutral oil with an alcohol such as methanol. A process that represents said type of process that can be cited is the process described in German Patent Application No. 4123928 (European Patent Application No. 0 523 767), which involves the continuous use of a basic homogeneous catalyst.

That type of process has a number of disadvantages. Once the reaction is over, the excess catalyst essentially present in the glycerin phase in the form of alcoholates and soaps must be neutralized, then the water and monoalcohol (methanol) must be removed by evaporation. The monoalcohol (methanol) that evaporates usually has to be distilled. For the ester fraction, traces of alkaline compounds are removed by washing with water and drying.

In general, in processes using a homogeneous catalysis technique, to reach the desired specifications for the glycerin and the ester, a chain of complex and laborious treatments must be implemented, which does not produce a glycerin that is completely free of traces of alkali salts, substantially reducing the price of this high added value co-product.

Other processes employ heterogeneous catalysts, such as that described in European Patent Application No. 0 924 185. That process is a three-step process using a heterogeneous catalyst:

a first step (a) consists of reacting a vegetable oil with an excess of monoalcohol in the presence of a heterogeneous catalyst followed by eliminating the excess monoalcohol and separating the glycerin. That step produces a crude ester containing residual monoglycerides;

in a second step (b), the crude ester obtained undergoes re-esterification of the residual mono-glycerides into di- and tri-glycerides in the presence of a heterogeneous catalyst; and in a third step (c), the ester is evaporated off under reduced pressure, recycling the evaporation residue to the starting oil of step (a).

The principal disadvantage of such a process is the very high cost involved in vacuum distillation of the whole production yield. Further, the recycling also constitutes an extra cost. Finally, experiments have shown that even under much reduced pressure, the temperature at the bottom of the ester evaporation column is high, involving a high risk of residue degradation. Thus, the latter cannot be completely recycled and must be purged periodically, reducing the yield of the process.

Finally, French Patent No. 2 752 242 (=U.S. Pat. No. 5,908,946) describes a process for producing at least one fatty acid alkyl ester and high purity glycerin from a vegetable oil and an aliphatic monoalcohol in the presence, for example, of a catalyst comprising zinc aluminate, without describing the concatenation of individual steps in detail. It describes a system including the following steps:

transesterification of the oil, either batchwise or continuously, on a fixed bed or in an autoclave with at least 80–85%, preferably at least 90–95% conversion;

a first step for evaporating excess monoalcohol;

decanting the glycerin and the ester, said ester being recycled to a second step to undergo transesterification with a portion of the monoalcohol recovered from the first evaporation step;

a second monoalcohol evaporation step; and cold decanting and separating the glycerin from the alkyl ester.

Further, that patent mentions that the presence of water is deleterious as it encourages the formation of fatty acids, i.e., reagents, which may react to form soaps. It does not teach a procedure for limiting the water content, which in fact constitutes a much greater problem than that mentioned. Water actually inhibits the catalyst and its presence in the reaction medium beyond an amount of 1500 ppm by weight, preferably beyond 1000 ppm, is undesirable.

SUMMARY OF THE INVENTION

The present invention can satisfy this criterion by employing water/methanol separation steps at various stages of the process, which control the maximum amount of water in the reaction zones and also deliver very high purity glycerin. This latter point has a very substantial impact on the process costs, since the price of glycerin essentially depends on its purity. For refined glycerin (96% to 99.7% pure), average prices between 1998 and 1990 were $1.44/kg (1.64 euros/kg) in Europe, and $1.8/kg (2.05 euros/kg) in the United States.

BRIEF DESCRIPTION OF THE DRAWING

FIG. 1 is a flowsheet representing in a simplified way the process according to the invention

DETAILED DESCRIPTION OF THE INVENTION

The invention provides a process for producing alkyl esters derived from vegetable or animal oils, in particular methyl esters derived from rapeseed oil, which has the advantage of enjoying a yield that is very close to 100%, for producing very pure glycerin that is free of salts and finally, which produces no waste during normal operation.

In general, the process of the invention comprises employing a reaction for transesterification of a vegetable oil (usually rapeseed oil) or an oil of animal origin such as tallow, using an aliphatic monoalcohol (generally methanol) used in excess, with separation and recycling of the excess aliphatic monoalcohol to produce glycerin and the alkyl ester in the presence of a heterogeneous catalyst comprising zinc aluminate, for example, in a medium the water content of which is controlled both as regards the amount of water introduced by the reagents and the amount of water that accumulates in the aliphatic monoalcohol recycle loop.

In more detail, the process of the invention comprises a set of three balanced reactions occurring in parallel and which will be designated by the umbrella term "the reaction" in the remainder of the text.

Reaction 1

The oil (triglyceride) reacts with one molecule of monoalcohol (methanol) to produce one molecule of alkyl ester and a diglyceride.

Reaction 2

The diglyceride reacts with one molecule of monoalcohol (methanol) to produce one molecule of alkyl ester (methyl) and a monoglyceride.

Reaction 3

The monoglyceride reacts with one molecule of monoalcohol (methanol) to produce one molecule of alkyl ester (methyl) and one molecule of glycerin.

When biodiesel is to be produced, one of the principal constraints is to produce good conversion of the oil into the alkyl ester (methyl) (minimum 96.5%) to reach a maximum amount of monoglycerides of 0.8% by weight maximum. This implies many constraints on the process, in particular a large excess of monoalcohol (methanol) over the stoichiometric quantities, and at least two reaction steps between which the glycerin that is produced is eliminated to displace the equilibrium towards the production of the alkyl ester (methyl).

Thus, the invention consists in a process for producing alkyl esters of fatty acids and high purity glycerin, employing a set of transesterification reactions between a vegetable or animal oil and an aliphatic monoalcohol employing a heterogeneous catalyst comprising zinc aluminate, for example, characterized in that the water content in the reaction medium is controlled to a value that is below a given limiting value. The limiting value for the water content in the reaction medium is generally less than 1500 ppm, and preferably less than 1000 ppm. The set of transesterification reactions is generally carried out in at least two steps, the first step reacting the oil and the monoalcohol in a proportion of 20% to 80% by weight for the oil, and preferably in a proportion of 45% to 55% by weight for said oil, and the following steps reacting the alkyl ester formed during the first step with the monoalcohol in a proportion of 20% to 80%, preferably 45% to 55% by weight for the alkyl ester.

The reaction is generally carried out in the presence of a solid catalyst, for example comprising zinc aluminate (as described, for example in French Patent No. 2 752 242). The advantage of a heterogeneous catalyst over conventional homogeneous basic catalysts such as sodium hydroxide is that it can avoid the numerous steps for purifying the products formed which contain all of the catalyst. Thus, waste and their processing are avoided. As an example, the glycerin produced here is free of salts and is at least 95% and preferably 98% pure. In the present heterogeneous process, no polluted effluent is discharged. However, the present invention is also applicable to other solid as well as homogenous catalysts.

The reaction is generally carried out in one or more successive fixed bed reactors operated in upflow mode and in the liquid phase, each reactor being supplied with a mixture of oil (for example rapeseed oil) and monoalcohol (for example methanol) (first reactor) or mainly alkyl ester (methyl) and monoalcohol (methanol) (second reactor and optional subsequent reactors). The proportion of oil (for example rapeseed) or alkyl ester (methyl) is 20% to 80% and preferably 45% to 55% by weight at the inlet to each reactor. The optimum operating conditions are in the following ranges: $30 \times 10^5$ to $80 \times 10^5$ Pa and preferably $40 \times 10^5$ to $70 \times 10^5$ Pa as regards pressure, and 453K to 493K, preferably 463K to 483K as regards temperature. The water content in the reaction medium of each of the reactors is controlled to remain less than 1500 ppm, for example, preferably less than 1000 ppm by weight. At the outlet from the reactor or reactors, the alkyl ester (for example methyl) is obtained along with the co-product of the reaction, glycerin, also the excess aliphatic monoalcohol (for example methanol). The advantage of the process is that after evaporating off the monoalcohol (methanol) and separating the alkyl ester (methyl) and the glycerin by decanting, very pure high value products are obtained.

The invention will be better understood with reference to FIG. 1. In the described process, the monoalcohol employed is methanol.

In a preferred implementation of the invention as shown, the oil to be treated or feed oil is generally supplied from a plant for triturating grain from rapeseed or other vegetable oils such as palm oil, sunflower seed oil, soya oil, coprah oil, cottonseed oil or castor oil, as well as oil of animal origin such as tallow. The crude oil (A) is passed into a vacuum drier (1) to obtain a water content of less than 700 ppm by weight. The feed oil that has undergone this treatment will hereinafter be termed "dried oil".

The dried oil is mixed with recycled methanol (B). The mixture obtained contains 20% to 80%, preferably 45% to 55% by weight of oil and is compressed to a pressure of $62 \times 10^5$ Pa, for example, and heated to a temperature of 473K, for example (483K at the end of the service life of the catalyst). It passes from bottom to top in a tube reactor (2) containing a fixed bed of a catalyst comprising zinc aluminate in the form of extrudates. The HSV, i.e., the ratio between the hourly flow rate of the oil to be treated and the volume of the catalyst, is in the range 1.2 $h^{-1}$ to 0.1 $h^{-1}$, preferably in the range 0.6 $h^{-1}$ to 0.4 $h^{-1}$.

At least 90% by weight and generally at least 92% by weight of the oil is converted under these conditions. At the outlet from reactor (2), the mixture (C) contains the methyl ester, glycerin, methanol and slightly or unconverted glycerides (oil, di- and mono-glycerides). This mixture undergoes a depressurization phase, then the excess methanol is evaporated off in an evaporator (3) at a pressure of close to $2.5 \times 10^5$ Pa, for example. The methanol vapor is condensed in a condenser (4) then recycled to a knockout drum (5). This evaporation step is carried out so that the amount of residual methanol in the mixture is 5% to 25% by weight, preferably 10% to 20% by weight.

The presence in the mixture of a certain amount of methanol is important as this acts as a co-solvent for the methyl ester and the glycerin, which are naturally insoluble. The liquid (D) is then cooled to 323K and decanted in a decanter drum (6) to separate an upper phase (E) which is rich in methyl ester supplying the second reaction section, and a lower phase (F), which is rich in glycerin which must be treated in a specific manner.

Methanol from the knockout drum (5) is added to the methyl ester phase from the decanting drum (6) to once again obtain a mixture with a methyl ester mass content of 20% to 80% and preferably 45% to 55%. The mixture obtained is passed from bottom to top through a second reactor (7) which is identical to the first and which operates under substantially similar conditions to those of reactor (2). In the majority of cases, the operating conditions for reactors (2) and (7) will be practically identical, and the catalyst used in each of the reactors can be of the same nature. The conversion obtained at the outlet from the reactor (7) satisfies the specification for mono-glycerides in the methyl ester (H), which is a maximum of 0.8% by weight.

The methanol contained in the mixture of effluents from the reactor (7) is evaporated off in two steps in a group of evaporators (8).

The first evaporation step is generally carried out under the same conditions as that carried out in the evaporator (3), and the second evaporation step is carried out under vacuum to leave a maximum of 500 ppm by weight of methanol in the liquid (I), and preferably 200 ppm, which allows the methyl ester to be dried to a maximum of 200 ppm of water. After cooling and decanting the heavy effluent from the group of evaporators (8) in the decanter (10), a very pure glycerin phase (J) is obtained which can pass directly to the battery limits, and a methyl ester phase (K) is obtained which undergoes the treatment described below. The methanol vapor from the group of evaporators (8) is condensed in a condenser (9) then recycled to the knockout drum (5).

The crude methyl ester (K) from the decanter (10) can be treated to satisfy the specification concerning the total glycerin content (free and potential), which is a maximum of 0.25% by weight.

The treatment of the crude methyl ester can be carried out in different ways:

As an example, the methyl ester can be passed into a coalescer (11) which eliminates the last traces of free glycerin, then optionally over adsorbent masses, generally ion exchange resins, which bind the dissolved glycerin, into an adsorber that is not shown in FIG. 1. The very pure glycerin (L) separated from the methyl ester is sent to the battery limits. The final methyl ester (M) is sent to the battery limits.

In other cases, the methyl ester can be treated using one or more steps for washing the ester with water.

The stream of glycerin (F) from the decanter drum (6) forming part of the first reaction section must be treated to attain a maximum methanol content of 5000 ppm by weight and a maximum NGOM (non-glycerin organic material) content of 1% by weight, which corresponds to the generally acceptable commercial level.

The methanol contained in stream (F) is generally evaporated in two steps. The first step is carried out at the bottom of the distillation column (12). The column (12) carries out two functions:

evaporation of methanol from the bottom glycerin to a 5% by weight methanol content; and water/methanol separation on the head plates. The overhead methanol contains a maximum of 800 ppm by weight of water, preferably 500 ppm.

This column is also supplied with a stream (N) of methanol vapor from evaporator (3) placed downstream of the first reactor (2). The methanol (O) leaving the head of the column (12) contains a maximum of 800 ppm by weight of water, preferably 500 ppm. The stream of methanol (O) is condensed in the condenser (13) then sent to the knockout drum (5). This operation is necessary to deconcentrate the water which enters the unit via the feed oil (A), drying of which is limited to 500 pm by weight, as pushing this step further would mean increasing the level of vacuum, which is expensive, or increasing the temperature and risking decomposition of part of the oil. Fresh methanol (T) provides the other entry point for water. By using the driest commercial methanol, i.e., grade A, the water content is guaranteed to be below 1000 ppm by weight. The water entering the system via these two routes accumulates in the methanol loop. As stated in the introduction, water inhibits the catalyst, and beyond a water content of 1000 ppm in the reaction mixture, the oil conversion drops markedly.

The glycerin (P) extracted from the bottom of the column (12), containing about 5% methanol, is sent to a vacuum evaporator (14). The methanol vapor is condensed in a condenser (15) and recycled to the column (12). The stream of glycerin (Q) withdrawn from the evaporator (14) containing about 3000 ppm of methanol is sent to the decanting drum (16). The methyl ester phase (R) issuing overhead from the decanting drum (16) is sent to the inlet to the group of evaporators (8) forming part of the second reaction section and purified glycerin (S) leaves to the battery limits.

Since the transesterification reaction consumes a portion of the methanol, fresh methanol (T) has to be introduced into the system.

A portion of this fresh methanol is sent to the methanol feed tank (5); the other portion can regenerate the ion exchange resins in the methyl ester treatment section, not shown in FIG. 1. To regenerate the resins saturated with glycerin, a stream of pure methanol is generally used. The resultant methanol which is contaminated with glycerin and a little methyl ester, is recycled to the process upstream of the glycerin treatment section. Then a stream of pure methyl ester from finished product storage is passed over the regenerated resins. The methyl ester contaminated with the methanol remaining adsorbed on the resins is recycled to the evaporation section of the second reaction section.

EXAMPLE

The oil used was a rapeseed oil and the methanol was commercial grade A methanol.

In the first reactor, the conversion is defined as the quantity of oil that has reacted, i.e. the oil completely converted to the methyl ester (total quantity of oil less the quantity of monoglycerides, diglycerides and triglycerides) over the total quantity of oil, i.e.: [50−(1.8+1.0+0.6)]/50= 93.2%. The amount of water in the first reactor was 1000 ppm.

In the second reactor, the conversion is related to the quantity of oil entering the first reactor by taking into account the monoglycerides and diglycerides that have reacted in the second reactor. The conversion is then: [50−(0.3+0.1+0)]/50=99.2%. The amount of water in the second reactor was 1200 ppm.

For the two reaction steps, the operating conditions were identical. The weight ratio of methanol to oil was 50/50 in the first reactor and the weight ratio of methanol to methyl ester was 48/49.6 in the second reactor.

The temperature was 473K. The pressure was $62 \times 10^5$ Pa. The oil/catalyst HSV was 0.5 $h^{-1}$.

Table 1 below shows a material balance for the first and second reaction zones.

TABLE 1

Material balance in the reaction zone

| Flow rate (kg/h) | Inlet reactor 1 | Outlet reactor 1 | Inlet reactor 2 | Outlet reactor 2 |
| --- | --- | --- | --- | --- |
| Methanol | 50.0 | 44.8 | 50.0 | 48.0 |
| Glycerin | 0.0 | 4.5 | 0.5 | 1.0 |
| Methyl ester | 0.0 | 47.3 | 46.2 | 49.0 |
| Monoglycerides | 0.0 | 1.8 | 1.8 | 0.8 |
| Diglycerides | 0.0 | 1.0 | 1.0 | 0.2 |
| Oil | 50.0 | 0.6 | 0.5 | 0.0 |
| Total | 100.0 | 100.0 | 100.0 | 100.0 |

To illustrate the advantage of operating in a controlled water content medium, Table 2 below shows, at the outlet from the second reaction step, the conversion as defined above as a function of the water content in the reaction medium in ppm. It can clearly be seen that the water content in the reaction medium has a direct and substantial influence on the conversion. With water content of less than 1500 ppm, and preferably less than 1000 ppm in the reaction medium, the conversion is at very high values, more than 99.2%.

TABLE 2

Influence of water content in feed on conversion to methyl ester (2$^{nd}$ step of catalysis)

| Amount of water in feed (ppm) | Conversion to ester (weight %) |
| --- | --- |
| 400 | 99.4 |
| 100 | 99.25 |
| 2500 | 98.9 |
| 5000 | 98.6 |
| 8000 | 98.5 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 02/04565, filed Apr. 11, 2002 are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for producing alkyl esters of fatty acids, and high purity glycerin, comprising conducting a set of transesterification reactions between a vegetable or animal oil and an aliphatic monoalcohol in the presence of a catalyst, said process comprising
 a) providing a dried oil to be treated;
 b) at least one step of transesterifying the dried vegetable or animal oil with an excess of said aliphatic monoalcohol, the proportion being of 20% to 80% by weight of the oil, to form an alkyl ester;
 c) at least one step of separating at least part of the excess of aliphatic monoalcohol in the form of vapor and removing glycerin;
 d) at least one step of transesterifying the alkyl ester resulting from step (b) with an excess amount of aliphatic monoalcohol, the proportion being of 20% to 80% by weight of the alkyl ester to form transesterified alkyl ester and a final excess of the aliphatic monoalcohol;
 e) and separating the final excess of the aliphatic monoalcohol to form the transesterified alkyl,
the improvement comprising separating water from at least part of the methanol vapor separated (in step (c)) and passing at least part of the resultant water-depleted methanol to at least one of steps (b) and (d), so as to control the water content in the transesterification reaction medium to a value of less than 1500 ppm.

2. A process according to claim 1, in which the catalyst comprises a heterogeneous catalyst.

3. A process according to claim 1, in which the water content in the reaction medium is less than 1000 ppm.

4. A process according to claim 2, in which the water content in the reaction medium is less than 1000 ppm.

5. A process according to claim 1, in which the set of transesterification reactions is carried out in at least two steps, the first step reacting the vegetable or animal oil and the monoalcohol in a proportion of 45% to 55% by weight of the oil and the subsequent steps reacting the alkyl ester formed after the first step with the monoalcohol in a proportion of 45% to 55% by weight of the alkyl ester.

6. A process according to claim 1, in which each of the reaction steps is carried out at a pressure of $30\times10^5$ to $80\times10^5$ Pa, at a temperature of 453K to 493K and at an HSV of 1.2 h$^{-1}$ to 0.1 h$^{-1}$.

7. A process according to claim 1, in which each of the reaction steps is carried out at a pressure of $40\times10^5$ to $70\times10^5$ Pa, at a temperature of 463K to 483K and at an HSV of 0.6 h$^{-1}$ to 0.4 h$^{-1}$.

8. A process according to claim 1, in which glycerin is obtained free of salts and has a purity of at least 95%.

9. A process according to claim 1, in which the feed oil comprises a vegetable oil derived from rapeseed oil, palm oil, sunflower seed oil, soya oil, coprah oil, cottonseed oil, castor oil, or tallow.

10. A process according to claim 1, in which resultant alkyl ester from a final reaction step is separated on regeneratable adsorbent masses in order to remove the glycerin contained therein.

11. A process according to claim 10, in which separation is carried out using ion exchange resins.

12. A process according to claim 1, in which the alkyl ester obtained from the last reaction step is washed with water in a plurality of washing steps to remove the glycerin contained therein.

13. A process according to claim 2, wherein the heterogeneous catalyst is zinc aluminate.

14. A process according to claim 8, wherein the glycerin has a purity of at least 98%.

15. A process according to claim 1, wherein the monoalcohol is methanol.

16. A process according to claim 15, wherein reactions are conducted with a vegetable oil feed comprising rapeseed oil and the reaction conditions are sufficient to provide a conversion to methyl ester of at least 96.5%.

17. A process according to claim 5, wherein the monoalcohol is methanol.

18. A process according to claim 6, wherein the monoalcohol is methanol.

19. A process according to claim 15, wherein the catalyst is zinc aluminate.

20. A process according to claim 1, wherein said separating of said water is conducted in an upper zone of a distillation column and further comprising passing separated glycerin to a lower zone of said distillation column to separate aliphatic monoalcohol from said glycerin and recovering resultant glycerin from said distillation column.

21. A process according to claim 20, wherein the monoalcohol is methanol.

* * * * *